United States Patent
Nishikawa et al.

(10) Patent No.: US 7,951,962 B2
(45) Date of Patent: May 31, 2011

(54) ORGANIC SEMICONDUCTOR COMPOUND, ORGANIC SEMICONDUCTOR THIN FILM, ORGANIC SEMICONDUCTOR COATING LIQUID, ORGANIC THIN FILM TRANSISTOR, METHODS FOR PRODUCING BIS(BENZO[4,5] THIENO)[2,3-B:3'2'-E][1,4]DITHIN AND BIS(BENZO [4,5]THIENO)[2,3-B:2'3'-E][1,4]DITHIIN

(75) Inventors: Takao Nishikawa, Shiojiri (JP); Satoshi Ogawa, Morioka (JP)

(73) Assignee: Seiko Epson Corporation, Tokyo (JP)

( * ) Notice: Subject to any disclaimer, the term of this patent is extended or adjusted under 35 U.S.C. 154(b) by 904 days.

(21) Appl. No.: 11/850,357

(22) Filed: Sep. 5, 2007

(65) Prior Publication Data
US 2008/0076935 A1    Mar. 27, 2008

(30) Foreign Application Priority Data

Sep. 21, 2006 (JP) .................. 2006-256399
Jun. 1, 2007 (JP) .................. 2007-147380

(51) Int. Cl.
*C07D 339/08* (2006.01)

(52) U.S. Cl. ........................................................ 549/15

(58) Field of Classification Search ..................... 549/15
See application file for complete search history.

(56) References Cited

FOREIGN PATENT DOCUMENTS
WO    WO 03/016599 A1    2/2003

OTHER PUBLICATIONS

Yamamoto, Tatsuya et al., "Selective Synthesis, Structure and Oxidation Properties of Isomeric 1, 4-dithiins Fused to Two Benzo[b]thiophenes," Tetrahedron Letters, vol. 45, p. 7943-7946 (2004).

*Primary Examiner* — Taofiq A Solola
(74) *Attorney, Agent, or Firm* — Oliff & Berridge, PLC

(57) ABSTRACT

An organic semiconductor compound is represented by a general formula 1:

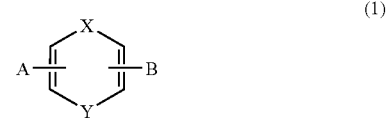

(1)

wherein A and B each are an aromatic ring with a conjugated electron system and X and Y each are $DR_2$, ER or G in which D denotes any of C, Si, Ge and Sn, E denotes any of N, P, As and Bi, G denotes any of O, S, Se and Te and R denotes any of H, an alkyl group and an aryl group.

2 Claims, 5 Drawing Sheets

ORGANIC SEMICONDUCTOR COMPOUND, ORGANIC SEMICONDUCTOR THIN FILM, ORGANIC SEMICONDUCTOR COATING LIQUID, ORGANIC THIN FILM TRANSISTOR, METHODS FOR PRODUCING BIS(BENZO[4,5]THIENO)[2,3-B:3'2'-E][1,4]DITHIN AND BIS(BENZO[4,5]THIENO)[2,3-B:2'3'-E][1,4]DITHIIN

The entire disclosure of Japanese Patent Application Nos: 2006-256399, filed Sep. 21, 2006 and 2007-147380, filed Jun. 1, 2007 are expressly incorporated by reference herein.

BACKGROUND

1. Technical Field

The present invention relates to an organic semiconductor compound having particularly good solvent solubility and semiconductor characteristics, an organic semiconductor thin film, an organic semiconductor coating liquid and an organic thin film transistor. In addition, the invention relates to novel methods for producing bis(benzo[4,5]thieno)[2,3-b:3'2'-e][1,4]dithiin and bis(benzo[4,5]thieno)[2,3-b: 2'3'-e][1,4]dithiin.

2. Related Art

Recently, as semiconductor materials for thin film transistors (TFTs), much attention has been focused on organic semiconductor materials. The organic semiconductor material facilitates the formation of a thin film by using a simple and easy technique such as spin coating or vacuum vapor deposition. As another advantage using the organic semiconductor material for TFTs, temperature during film forming process can be reduced compared to the formation of a well-known TFT made of amorphous or polycrystalline silicon. Low temperature process allows the formation of a thin film even on a low heat-resistant plastic substrate. Consequently, weight and cost reductions of a display can be realized, and moreover, for example, diversified application possibilities by taking advantage of flexibility of the plastic substrate will be expected.

Carrier mobility is among important physical parameters of the organic semiconductor material. Due to inherently weak intermolecular interaction force thereof, the organic semiconductor material strongly exhibits the properties of molecules themselves and in particular, the carrier mobility thereof is small compared to inorganic semiconductor materials. This weakness has been a significant impediment to practical application thereof.

The organic semiconductor material is roughly classified into two groups, low molecules and high molecules. The low molecular materials that have been developed include hydrocarbons such as acenes (see an example of patent related art below), sulfur-containing compounds such as thiophenes, and nitrogen-containing compounds such as phthalocyanines. The high molecules developed include poly(9,9-dioctylfluorene-co-bithiophene) (F8T2) and poly(3-hexylthiophene) (P3HT).

PCT Application No. WO 03/016599 is the above-mentioned example of patent related art.

Tetrahedron Lett., Vol. 45, 7943-7946 (2004) is an example of non-patent related art.

In general, the low-molecular materials offer higher mobility than the high-molecular materials, but lack a high solvent solubility, thereby resulting in poor productivity. Improving their solvent solubility allows employment of an inkjet method or the like, which can lead to cost reduction. Accordingly, there has been a demand for a novel low-molecular organic semiconductor material that can offer improved carrier mobility and solvent solubility.

SUMMARY

An advantage of the present invention is to provide a novel low-molecular organic semiconductor compound having high carrier mobility and solvent solubility, an organic semiconductor thin film and an organic semiconductor coating liquid both including the organic semiconductor compound.

Another advantage of the invention is to provide an organic thin film transistor using the novel organic semiconductor compound as an active layer.

Still another advantage of the invention is to provide novel methods for producing bis(benzo[4,5]thieno)[2,3-b:3'2'-e][1, 4]dithiin and bis(benzo[4,5]thieno)[2,3-b:2'3'-e][1,4]dithiin.

An organic semiconductor compound according to a first aspect of the invention is represented by a general formula 1:

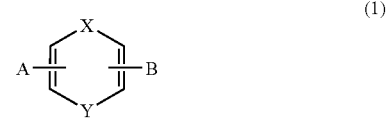

(1)

wherein A and B each are an aromatic ring with a conjugated electron system and X and Y each are $DR_2$, ER or G in which D denotes any of C, Si, Ge and Sn, E denotes any of N, P, As and Bi, G denotes any of O, S, Se and Te and R denotes any of H, an alkyl group and an aryl group.

The organic semiconductor compound according to the first aspect is a low-molecular compound and has a structure in which the aromatic rings A and B are connected by a center connecting ring therebetween. The aromatic rings A and B each have a conjugated electron system and thus have a planar structure, whereas the connecting ring without a conjugated electron system has a bending structure. Consequently, the electron-conjugated aromatic rings A and B are connected by the connecting ring with the bending structure to purposefully form a space for solvent molecules. This can improve the solvent solubility of the organic semiconductor compound.

Additionally, the aromatic rings A and B have the electron-conjugated system, that is, they have movable electrons. It is thus certain that the organic compound including the aromatic rings A and B connected by the connecting ring has semiconductor characteristics as a whole. Furthermore, in the organic semiconductor compound according to the first aspect, the aromatic rings A and B each are connected to the connecting ring by sharing edges therebetween, which means bonding between the two atoms. As a result, although the connecting ring itself does not have a conjugated electron system, interaction takes place between the connecting ring and each of the aromatic rings A and B, which can increase effects of the conjugation systems of both the aromatic rings A and B.

Furthermore, when X and Y are selected from group 15 or 16 elements, the connecting ring can be changed to have a conjugated electron system due to single or double electron oxidation (electron release) after film formation. In order to induce the change, it is also effective to apply an external field (such as an electric field or a magnetic field) or energy (such as heat) after film formation, as needed. Thereby, the organic semiconductor compound can exhibit high solvent solubility, as well as can show high carrier mobility due to an extension of a pi-conjugation system after film formation.

Preferably, the organic semiconductor compound according to the first aspect is bis(benzo[4,5]thieno)[2,3-b:3'2'-e][1,4]dithiin represented by a structural formula 2:

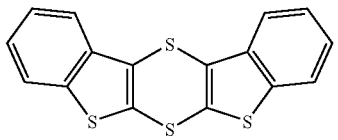

(2)

Alternatively, the organic semiconductor compound according to the first aspect is preferably bis(benzo[4,5]thieno)[2,3-b:2'3'-e][1,4]dithiin represented by a structural formula 3:

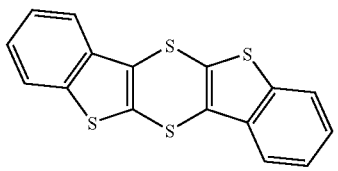

(3)

An organic semiconductor thin film according to a second aspect of the invention includes the organic semiconductor compound according to the first aspect. In this manner, the organic semiconductor thin film can have improved carrier mobility.

An organic semiconductor coating liquid according to a third aspect of the invention includes the organic semiconductor compound according to the first aspect and a solvent capable of dissolving the organic semiconductor compound. Since the organic semiconductor compound according to the first aspect shows high solvent solubility, the organic semiconductor coating liquid can be easily produced. Thus, applying the organic semiconductor coating liquid allows formation of an organic semiconductor thin film at a low cost.

Preferably, the above solvent includes at least one of a hydrocarbon, an alcohol, an ether, an ester, a halogen, a ketone, a nitrite, a benzene-toluene-xylene (BTX) and a non-proton polar solvent. This allows the solvent to dissolve the organic semiconductor compound.

An organic thin film transistor according to a fourth aspect of the invention includes the organic semiconductor thin film according to the second aspect as an active layer. In this manner, the organic semiconductor thin film transistor can improve carrier mobility and productivity.

In addition, according to a fifth aspect of the invention, there is provided a method for producing bis(benzo[4,5]thieno)[2,3-b:3'2'-e][1,4]dithiin represented by a structural formula 4:

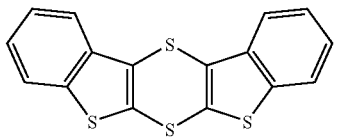

(4)

The method includes (i) dibrominating 3,3'-bis(benzo[b]thienyl)sulfide represented by a structural formula 5:

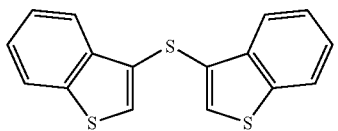

(5)

(ii) dianionizing the dibromo compound and (iii) adding sulfur dichloride to react with the dianionic compound.

The above method can increase a yield of the bis(benzo[4,5]thieno)[2,3-b:3'2'-e][1,4]dithiin.

In addition, according to a sixth aspect of the invention, there is provided a method for producing bis(benzo[4,5]thieno)[2,3-b:2'3'-e][1,4]dithiin represented by a structural formula 6:

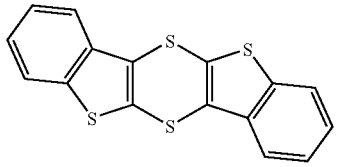

(6)

the method includes producing 2,3'-bis(benzo[b]thienyl)sulfide represented by a structural formula 7:

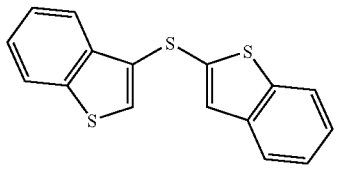

(7)

via a production of 2-acetylthiobenzo[b]thiophene represented by a structural formula 8:

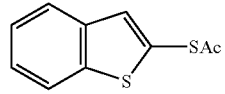

(8)

from benzo[b]thiophene represented by a structural formula 9:

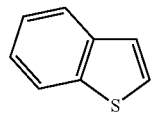

(9)

The above method can increase a yield of the 2,3'-bis(benzo[b]thienyl)sulfide, thereby also increasing a yield of the bis(benzo[4,5]thieno)[2,3-b:2'3'-e][1,4]dithiin as a final product.

In addition, according to a seventh aspect of the invention, there is provided a method for producing bis(benzo[4,5]thieno)[2,3-b:2'3'-e][1,4]dithiin represented by a structural formula 10:

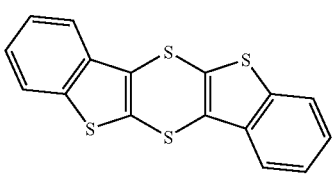

(10)

The method includes (i) dibrominating 2,3'-bis(benzo[b]thienyl)sulfide represented by a structural formula 11:

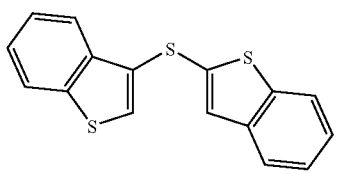

(11)

(ii) dilithiating the dibromo compound and (iii) performing sulfurization and cyclization of the dilithio compound.

In this manner, the above bis(benzo[4,5]thieno)[2,3-b:2'3'-e][1,4]dithiin can be produced at a low cost.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
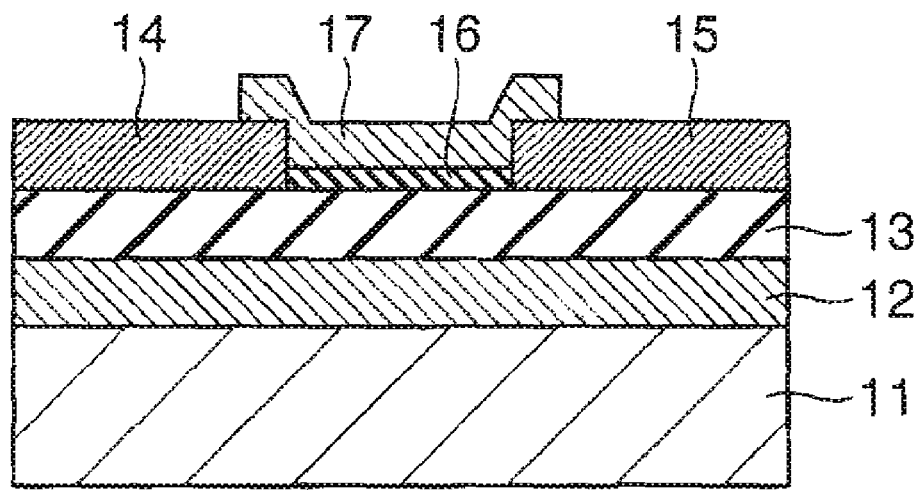
FIG. 1 is a sectional view of an organic thin film transistor according to an embodiment of the invention.

Embodiments of the invention will be described hereinafter with reference to the drawings.

Organic Semiconductor Compound

An organic semiconductor compound according to an embodiment of the invention is represented by a general formula 12:

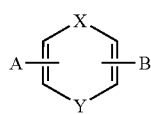

(12)

In the above formula, A and B each are an aromatic ring with a conjugated electron system; and X and Y each are $DR_2$, ER or G in which D denotes any of G, Si, Ge and Sn, E denotes any of N, P, As and Bi, G denotes any of O, S, Se and Te and R denotes any of H, an alkyl group and an aryl group.

The above organic compound is a condensed ring compound in which the two aromatic rings A and B each having the conjugated electron system are connected by a connecting ring represented by a general formula 13:

(13)

In other words, the organic semiconductor compound according to the present embodiment is the condensed ring compound formed by edge sharing between the connecting ring and each of the electron-conjugated aromatic rings, which means bonding between the two atoms.

It is only necessary for the aromatic rings A and B to have a pi-electron conjugated system. They may be composed only of a hydrocarbon or may contain elements other than a hydrocarbon. In addition, the aromatic rings A and B may each have a single ring, or two or more rings. Furthermore, those rings may be the same or different from each other. Examples of the aromatic rings A and B include those represented by the following formulas 14:

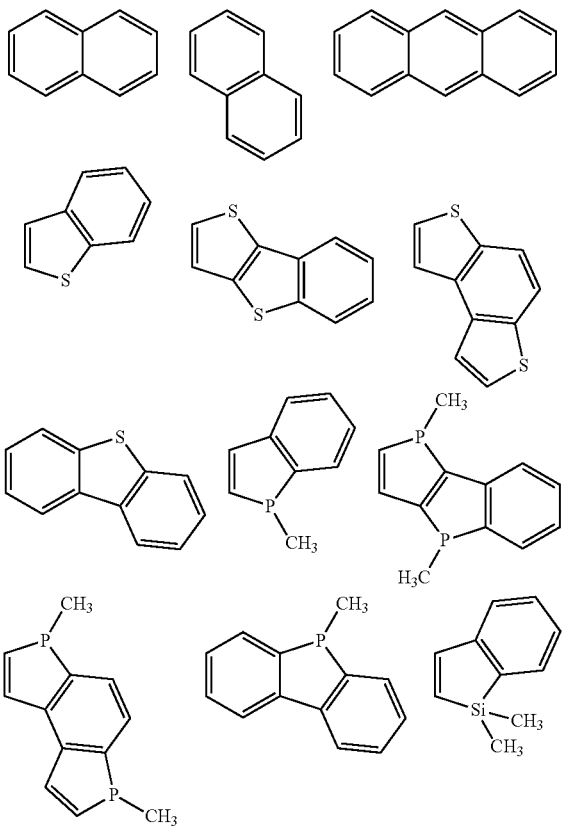

(14)

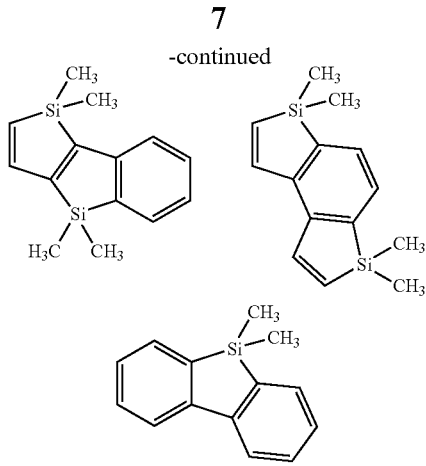
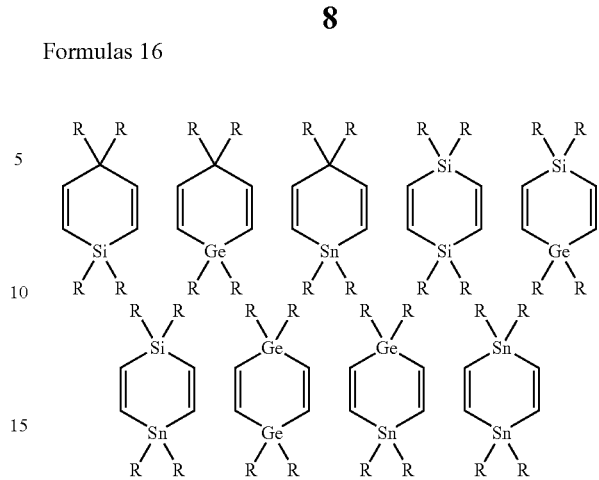

Formulas 16

The X and Y of the connecting ring are made of $DR_2$, ER or G. Symbol D denotes C, Si, Ge or Sn from group 14 elements; E denotes N, P, As or Bi from group 15 elements; and G denotes O, S, Se or Te from group 16 elements. R denotes H (hydrogen), an alkyl group or an aryl group. When the X and Y of the connecting ring are made of the above ER or G, examples of the connecting rings may be represented by the following formulas 15:

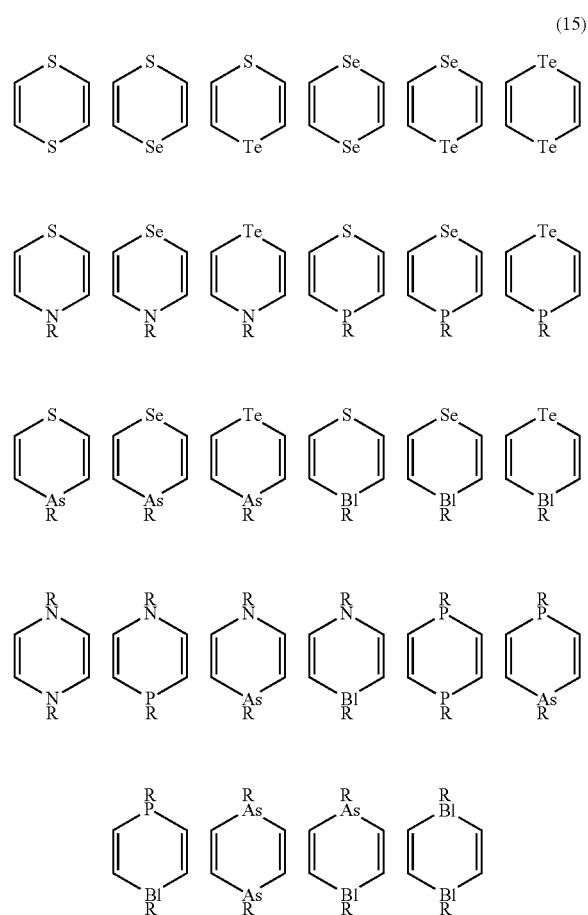

(15)

When the X and Y of the connecting ring are made of the $DR_2$, structural examples thereof may be as below. Symbol R denotes one of H (hydrogen), an alkyl group and an aryl group.

A description will be given of effects of the above organic semiconductor compound according to the embodiment. The organic semiconductor compound is a low-molecular organic compound. In the compound according to the embodiment, the aromatic rings A and B have a pi-electron conjugated system and thus have a planar structure. Meanwhile, the connecting ring does not have a pi-electron conjugated system and thus has a bending structure. The electron-conjugated aromatic rings A and B are connected by the connecting ring with the bending structure, whereby a space for solvent molecules is formed purposefully. This results in improvement in solvent solubility of the organic semiconductor compound according to the embodiment.

In addition, since the aromatic rings A and B have the pi-electron conjugated system, they have movable electrons. Accordingly, the organic compound composed of the aromatic rings A and B connected by the connecting ring can be regarded as having semiconductor characteristics as a whole. Furthermore, in the organic semiconductor compound according to the embodiment, the aromatic rings A and B each are connected to the connecting ring in such a manner as to share edges therebetween. As a result, even though the connecting ring itself is not a pi-electron conjugated ring, interaction occurs between the ring and each of the aromatic rings A and B. This can increase effects of the conjugation systems of both the aromatic rings A and B.

Furthermore, selecting the X and Y from the group 15 or 16 elements allows conversion of the connecting ring into a conjugated ring by a single or double electron oxidation (electron discharge) after film formation. Additionally, in order to induce the change, it is also effective to apply an external field such as an electric field or a magnetic field or energy such as heat after film formation as needed. Thereby, the organic semiconductor compound according to the embodiment can exhibit high solvent solubility, as well as can show carrier mobility by extension of the pi-conjugation system after film formation.

Organic Semiconductor Thin Film

An organic semiconductor thin film according to the embodiment includes mainly the organic semiconductor compound described above. After a thin film is formed using the above organic semiconductor compound, the film is patterned so as to provide the organic semiconductor thin film.

The organic semiconductor thin film is formed, for example, by a chemical vapor deposition (CVD) method, vacuum vapor deposition or a coating method. Preferably, the thin film is formed by a simple and easy coating method. In the coating method, after applying a solution obtained by dissolving the above organic semiconductor compound into a solvent, a post-processing (e.g. heating, infrared radiation or ultrasonic wave application) is performed on the applied film as needed, whereby the organic semiconductor thin film can be provided. In this case, examples of the coating method may be spin coating, casting, micro gravure coating, gravure coating, bar coating, roll coating, wire-bar coating, dip coating, spray coating, screen printing, flexo printing, offset printing, an inkjet method and micro-contact printing, of which either a single method or a combination of two or more methods may be used.

Among them, it is preferable to use the inkjet method to form the organic semiconductor thin film. In the inkjet method, without forming a resist mask, the organic semiconductor thin film can be formed only in a desired region. Accordingly, the amount of a material to be used can be reduced, thereby also reducing its production cost. Furthermore, the inkjet method requires neither a photo resist material, chemical agents such as a developing agent and a stripping agent, nor plasma treatments such as oxygen plasma and $CF_4$ plasma. Therefore, any change (e.g. being doped) or deterioration does not occur in the characteristics of the organic semiconductor material.

Organic Semiconductor Coating Liquid

An organic semiconductor coating liquid according to the embodiment includes the above-described organic semiconductor compound and a solvent for dissolving the organic semiconductor compound. An amount of the organic semiconductor compound included in the coating liquid is adjusted by a coating method and a thickness of an intended organic semiconductor thin film. In the case of using the inkjet method, the amount and kind of a solvent are adjusted to obtain a viscosity and a contact angle appropriate for ejection from a liquid droplet ejection apparatus.

The solvent for dissolving the organic semiconductor compound material according to the embodiment may be a hydrocarbon, an alcohol, an ether, an ester, a halogen, a ketone, a nitrite, the BTX, a non-proton polar solvent or a mixture solvent thereof. The hydrocarbon may be hexane, heptane, octane or cyclohexane, for example. The alcohol may be methanol, ethanol, (iso-)propanol or butanol. The ether may be diethyl ether, tetrahydrofuran or dioxane and the ester may be ethyl acetate or butyl acetate. The halogen may be dichloromethane or chloroform and the ketone may be acetone or methyl ethyl ketone. The nitrile may be acetonitrile or methyl nitrile. The BTX is a mixture of benzene, toluene and xylene. The non-proton polar solvent may be dimethylsulfoxide (DMSO), dimethylformamide (DMF) or hexamethylphosphoramide (HMPA).

Organic Thin Film Transistor

FIG. 1 is a sectional view of an organic thin film transistor according to the embodiment.

An organic thin film transistor 10 shown in FIG. 1 includes a gate electrode 12 disposed on a substrate 11, a gate insulation film 13 disposed on the gate electrode 12, a source electrode 14 and a drain electrode 15 disposed on the gate insulation film 13, an organic semiconductor thin film 17 disposed above the gate insulation film 13 between the source electrode 14 and the drain electrode 15, through an intermediary of a modifying film 16.

The above organic semiconductor transistor 10 is a thin film transistor having the gate electrode 12, which is disposed not on the organic semiconductor thin film 17 acting as an active layer but on the substrate 11. In other words, it is a thin film transistor having a bottom-gate structure. However, the transistor 10 may have an alternative structure. For example, it may be a thin film transistor with a structure in which the organic semiconductor thin film 17 is disposed not on the gate electrode 12 but on the substrate 11. That is, the transistor 10 may be a top-gated thin film transistor.

Hereinafter, individual sections included in the organic thin film transistor 10 will be explained sequentially.

The substrate 11 supports individual layers (sections) of the organic thin film transistor 10. The substrate 11 may be, for example, a glass substrate, a plastic substrate (resin substrate) made of polyimide, polymethyl methacrylate (PMMA), polycarbonate (PC), polyether sulfone (PES), aromatic polyether (liquid crystal polymer) or the like, a quartz substrate, a silicon substrate or a garium arsenide (GaAs) substrate. In order to make the organic thin film transistor 10 flexible, a resin substrate may be selected as the substrate 11.

The gate electrode 12 may be made of a conductive material such as a metal or a metallic oxide, or it may be a conductive region formed by introducing an impurity into the substrate 11. Examples of the material thereof include Ag, Pd, Pt, Au, W, Ta, Mo, Al, Cr, Ti, Cu, Ni, an alloy of any combination thereof, indium tin oxide (ITO), indium oxide (IO), indium zinc oxide (IZO), antimony tin oxide (ATO) and stannic oxide ($SnO_2$). Among them, either one kind or a combination of two or more kinds of materials may be used.

The gate insulation film 13 insulates the gate electrode 19 from the source electrode 14 and the drain electrode 15. The gate insulation film 13 may be made of either an inorganic material or an organic material (particularly, an organic polymeric material). The inorganic material to be used as the gate insulation film 13 may be a silicon oxide. The organic polymeric material for the gate insulation film 13 may be an acrylic resin such as polystyrene, polyimide, polyamidoimide, polyvinyl phenylene, polycarbonate (PC) or polymethyl methacrylate (PMMA), a fluorocarbon resin such as polytetrafluoroethylene (PTFE), a phenol resin such as polyvinylphenol or novolac resin, or an olefin resin such as polyethylene, polypropylene, polyisobutylene or polyisobutene. Among them, either one kind of material or a combination of two or more kinds of materials may be used. The gate insulation film 13 is not restricted to a single-layered film and may be a film formed by laminating multiple layers.

The material of each of the source electrode 14 and the drain electrode 15 is not specifically restricted as long as it has conductivity. The material may be, for example, a conductive material such as Pd, Pt, Au, W, Ta, Mo, Al, Cr, Ti, Cu, or an alloy of any thereof, a conductive oxide such as ITO, FTO, ATO or $SnO_2$, a carbon material such as carbon black, carbon nanotube or fullerene, a conductive polymeric material such as polyacetylene, polypyrrole, polythiophene (e.g. poly-ethylenedioxythiophene (PEDOT), polyaniline, poly(p-phenylene), polyfluorene; polycarbazole, polysilane or a derivative of any thereof. Among them, either one kind of material or a combination of two or more kinds of materials may be used. The above conductive high polymeric material is usually used after conductivity is given thereto by predoping with a high polymer such as iron oxide, iodine, mineral acid, organic acid or polystyrene sulfonic acid. Particularly among them, it is preferable to use a material mainly made of Ni, Cu, Co, Au, Pd or an alloy of any thereof to form the source electrode 14 and the drain electrode 15.

The modifying film 16, which promotes adhesion between the organic semiconductor thin film 17 and the gate insulation film 13, is disposed as needed. The modifying film 16 may be made of hexamethyl silazane, for example.

The organic semiconductor thin film 17 includes the organic semiconductor compound according to the embodiment. A (mean) thickness of the organic semiconductor thin film 17 is in a range of preferably approximately 0.1 to 1000 nm, more preferably approximately 1 to 500 nm and still more preferably approximately 10 to 100 nm.

In the above organic thin film transistor 10, changing a voltage applied to the gate electrode 12 allows control of an amount of electric current flown between the source electrode 14 and the drain electrode 15. Specifically, in an OFF state in which no voltage is applied to the gate electrode 12, even if a voltage is applied between the source electrode 14 and the drain electrode 15, only a minute amount of electric current is flown therebetween because almost no carrier is present in the organic semiconductor thin film 17. Meanwhile, in an ON state in which a voltage is applied to the gate electrode 12, carriers are induced in a portion of the organic semiconductor thin film 17 that faces the gate insulation film 13, thereby resulting in formation of a channel region. In this situation, when voltage is applied between the source electrode 14 and the drain electrode 15, electrons flow through the channel region.

The amount of electric current required for driving a transistor is proportional to carrier (electron) mobility. The present embodiment uses a film containing the above-described organic semiconductor compound as the organic semiconductor thin film 17. Thereby, carrier mobility can be improved, which increases the electric current for driving the organic thin film transistor.

Method for Manufacturing Thin Film Transistor

FIGS. 2A to 2D are sectional views illustrating steps of a method for manufacturing the thin film transistor 10.

Figure 2A:
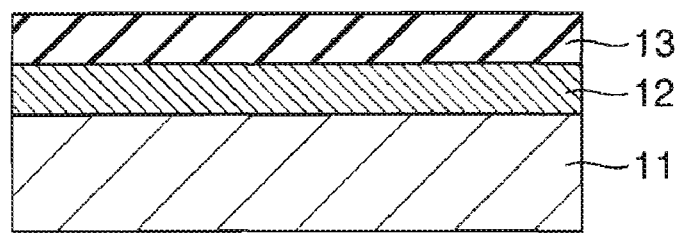
FIGS. 2A to 2D are sectional views showing steps for manufacturing the organic thin film transistor according to the embodiment.

As shown in FIG. 2A, the gate electrode 12 is formed into a desired pattern on the substrate 11. The gate electrode 12 may be formed using an inkjet method ejecting a liquid material containing conductive particles or a lift-off method. Alternatively, after formation of a conductive film, etching may be performed on the conductive film using a resist mask formed by lithography to form the gate electrode 12. When using a silicon substrate as the substrate 11, an impurity may be introduced into the silicon substrate to form the gate electrode 12.

Next, the gate insulation film 13 is formed on the gate electrode 12. The gate insulation film 13 may be, for example, formed as follows. First, a solution containing insulation material or its precursor is applied on the gate electrode 12 by a coating method. Then, as needed, a post-processing (e.g. heating, infrared radiation or ultrasonic wave application) is performed on the coat film. Alternatively, the inkjet method may be used to form the gate insulation film 13. Furthermore, alternatively, thermal oxidation may be performed on a surface of the silicon substrate to form the gate insulation film 13 made of silicon oxide.

Figure 2B:
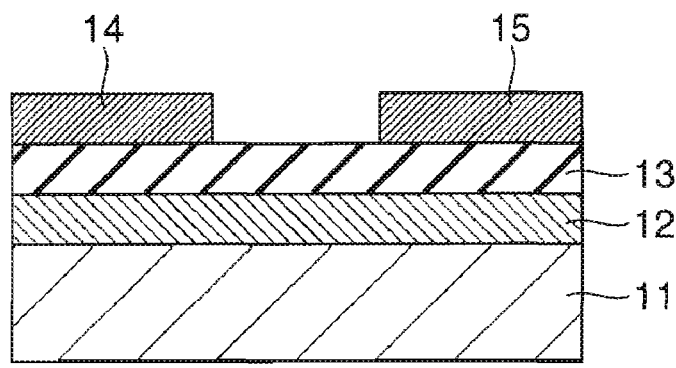

Next, as shown in FIG. 2B, after forming the conductive film on the gate insulation film 13, patterning is performed on the conductive film to form the source electrode 14 and the drain electrode 15.

For example, the conductive film may be formed by a chemical vapor deposition (CVD) method such as plasma CVD, thermal CVD or laser CVD, a dry plating method such as vacuum vapor deposition, sputtering or ion plating, a wet plating method such as electroplating, immersion plating or electroless plating, a spray method, a sol-gel method or a metal organic decomposition (MOD) method.

In the step of patterning the conductive film, a resist mask is formed on the conductive film by lithography and then etching is performed on the conductive film using the resist mask. The etching may be performed by either one method or a combination of two or more methods selected from physical etching methods such as plasma etching, reactive etching, beam etching and photo-assist etching, as well as a chemical etching method such as wet etching. Among them, wet etching is preferably used. Then, the resist mask is removed.

Instead of the above method, a lift-off method may be used to form the source electrode 14 and the drain electrode 15. Specifically, on the substrate 11 is formed a resist mask having openings corresponding to shapes of the electrodes 14 and 15 and then a conductive film is deposited on the substrate 11 with the resist mask thereon. After that, by stripping the resist mask, the conductive film is left only at the openings of the resist mask, whereby the source electrode 14 and the drain electrode 15 can be formed.

Figure 2C:
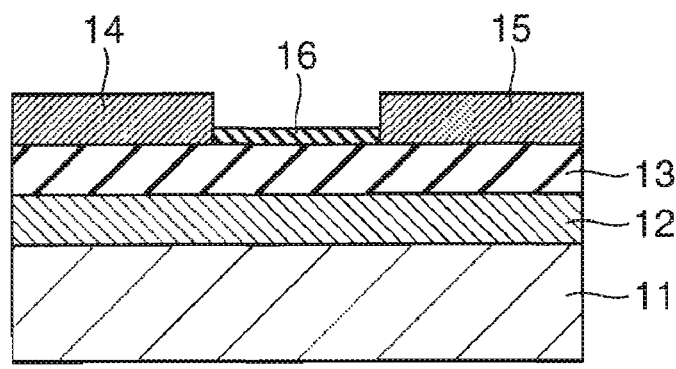

Then, as shown in FIG. 2C, the modifying film 16 is formed on a surface of the gate insulation film 13 exposed between the source electrode 14 and the drain electrode 15. For example, a layer of hexamethyl disilazane may be formed as the modifying film 16 by a CVD method.

Figure 2D:
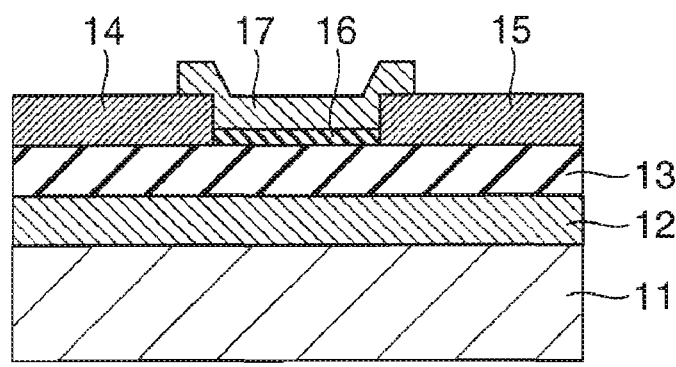

Next, as shown in FIG. 2D, on the modifying film 16 is formed the organic semiconductor thin film 17 using the organic semiconductor compound according to the embodiment.

For example, the organic semiconductor thin film 17 may be formed by a CVD method, vacuum vapor deposition or a coating method, and preferably by a simple and easy coating method. In the coating method, after coating is performed using a solution obtained by dissolving the above organic semiconductor compound into a solvent to form a film, a post-processing (e.g. heating, infrared radiation or ultrasonic wave application) is performed on the obtained film as needed so as to form the organic semiconductor thin film 17.

Among coating methods, the inkjet method is preferable to form the organic semiconductor thin film. In the inkjet method, without forming a resist mask, the organic semiconductor thin film can be formed only in a desired region. Thus, the amount of a material to be used can be reduced, thereby resulting in reduction in production cost. In addition, the inkjet method requires neither a photo resist material, chemical agents such as a developing agent and a stripping agent, nor plasma treatments such as oxygen plasma and $CF_4$ plasma. Therefore, any change (e.g. being doped) or deterioration does not occur in the characteristics of the organic semiconductor material.

In the manner as described above, the organic thin film transistor 10 according to the embodiment can be obtained.

In the method for manufacturing the above organic thin film transistor 10, using the organic semiconductor compound having high solvent solubility, the organic semiconductor thin film 17 can be formed by a coating method such as the inkjet method. Accordingly, the organic thin film transistor 10 can be manufactured at a low cost.

The above-described organic thin film transistor 10 is used on an active-matrix substrate for various displays, for example. The display may be an electrophoretic display, a liquid crystal display, an organic EL display, an inorganic EL display or the like.

The display may be used as a display section of various electronic apparatuses such as a TV set, an electronic paper, a videotape recorder of a viewfinder type or monitor-direct-view type, a car navigation system, a pager, an electronic organizer, an electronic portable calculator, an electronic newspaper, a word processor, a personal computer, a workstation, a TV phone, a point-of-sale (POS) terminal and an apparatus with a touch panel.

Next, detailed examples of the present embodiment will be shown below, although the invention is not restricted thereto.

Organic Semiconductor Compound

Each of the detailed examples used a benzo[b]thiophene ring as the aromatic rings A and B, with a 1,4-dithiin used as the connecting ring. Specifically, the organic semiconductor compound of each example is a condensed ring compound made of two benzo[b]thiophene rings and a 1,4-dithiin ring.

The condensed compound has two structural isomers, which are a syn-type bis(benzo[4,5]thieno)[2,3-b: 3'2'-e]-[1,4]dithiin represented by a structural formula 17:

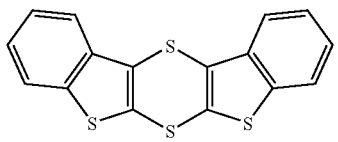

(17)

and an anti-type bis(benzo[4,5]thieno)[2,3-b: 2'3'-e][1,4] dithiin represented by a structural formula 18:

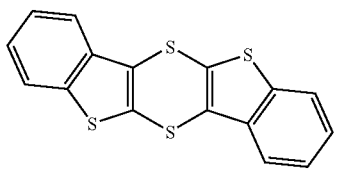

(18)

Example 1

In an example 1 below, the organic thin film transistor was manufactured using the syn-type bis(benzo[4,5]thieno)[2,3-b: 3'2'-e][1,4]dithiin to evaluate characteristics thereof. A description will be given of a method for manufacturing the thin film transistor of the example 1 with reference to FIGS. 2A through 3.

Method for Manufacturing Organic Thin Film Transistor

The substrate 11 shown in FIG. 2A is a monocrystal silicon substrate (silicon wafer) having an impurity-doped region. The region that was conductively doped with an impurity was used as the gate electrode 12.

Next, as shown in FIG. 2B, on the surface of the substrate 11 was formed the gate insulation film 13 made of a thermal oxide film having a thickness of 300 nm. Next, patterns of the source electrode 14 and the drain electrode 15 made of gold (Au) were formed by a vacuum deposition method and lithography. A distance (channel length) between both electrodes 14 and 15 was set to be 50 μm.

Then, as shown in FIG. 2C, the modifying film 16 was formed on the gate insulation film 13 by a chemical vapor phase growth method as a CVD method using hexamethyl disilazane (HMDS), which is a silane compound.

Next, as shown in FIG. 2D, the organic semiconductor thin film 17 was formed by vacuum vapor deposition using bis (benzo[4,5]thieno)[2,3-b: 3'2'-e][1,4]dithiin. The organic semiconductor thin film 17 was 100 nm in thickness.

Characteristics of the bottom-gate type organic thin film transistor (gate electrode: n-type silicon; channel length L: 50 μm; and channel width W: 2 mm) obtained by the above method were measured in a vacuum. Measurements were performed for both p- and n-channel conditions.

Experimentation Results

Figure 3:
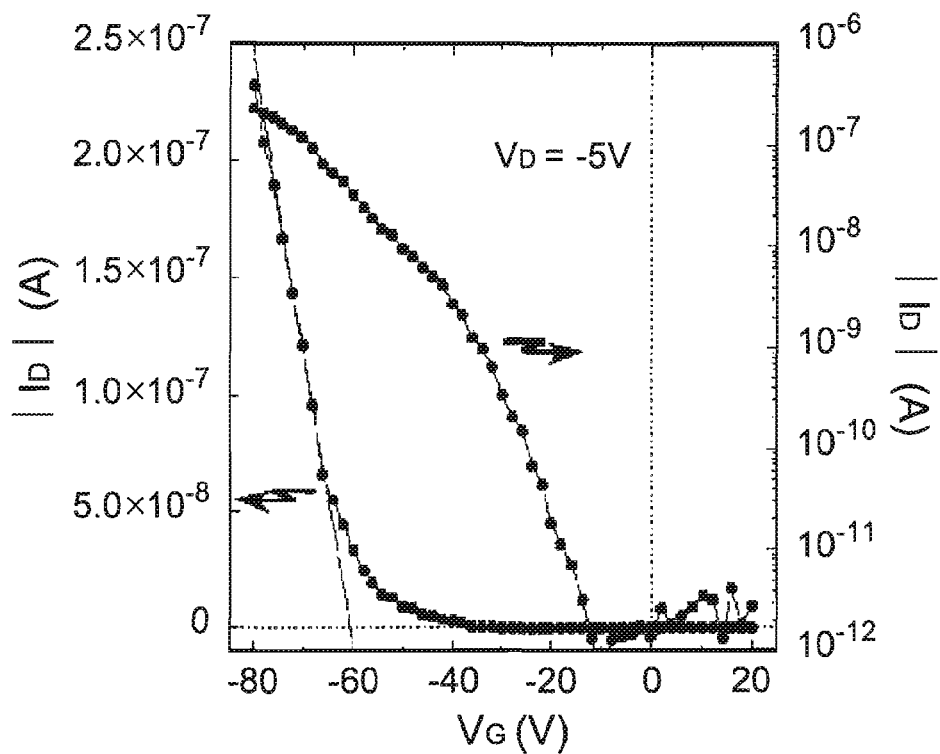
FIG. 3 is a graph showing the characteristics of drain current ($I_D$) versus gate voltage ($V_G$) of the organic thin film transistor obtained in an example 1 of the embodiment.

FIG. 3 shows the characteristics of drain current ($I_D$) versus gate voltage ($V_G$) obtained when a drain voltage ($V_D$) was fixed to be −5V, where the characteristics are plotted on both linear and logarithmic scales along the vertical axes. In FIG. 3, the vertical axis on the left is a linear vertical axis and the vertical axis on the right is a logarithmic vertical axis.

Results shown in FIG. 3 demonstrated that bis(benzo[4,5] thieno)[2,3-b: 3'2'-e][1,4]dithiin has p-type semiconductor characteristics with a negative threshold voltage. Based on logarithmic plotting in the graph, an ON/OFF ratio of the device was approximately 105. Linear plotting therein showed that the mobility μ was $5.0 \times 10^{-3}$ cm$^2$/Vs and the threshold voltage Vth was −60.5V. Meanwhile, in the measurements for the n-channel condition, no semiconductor characteristics were observed. It was confirmed that the bis (benzo[4,5]thieno)[2,3-b: 3'2'-e][1,4]dithiin of the example 1 is soluble in the above-described solvent and exhibits higher solubility than well-known low-molecular organic semiconductor compounds.

Example 2

In an example 2, the organic thin film transistor was manufactured using the anti-type bis(benzo[4,5]thieno)[2,3-b: 2'3'-e][1,4]dithiin to evaluate the characteristics of the thin film transistor. Hereinafter, a method for manufacturing the thin film transistor of the example 2 will be described with reference to the drawings concerned.

Method for Producing Organic Semiconductor Monocrystal

In the example 2, first, a monocrystal was produced to be used as the organic semiconductor thin film 17. As an exemplary method, the so-called physical vapor transport method was used to produce the monocrystal made of the anti-type bis(benzo[4,5]thieno)[2,3-b: 2'3'-e][1,4]dithiin.

Figure 4:
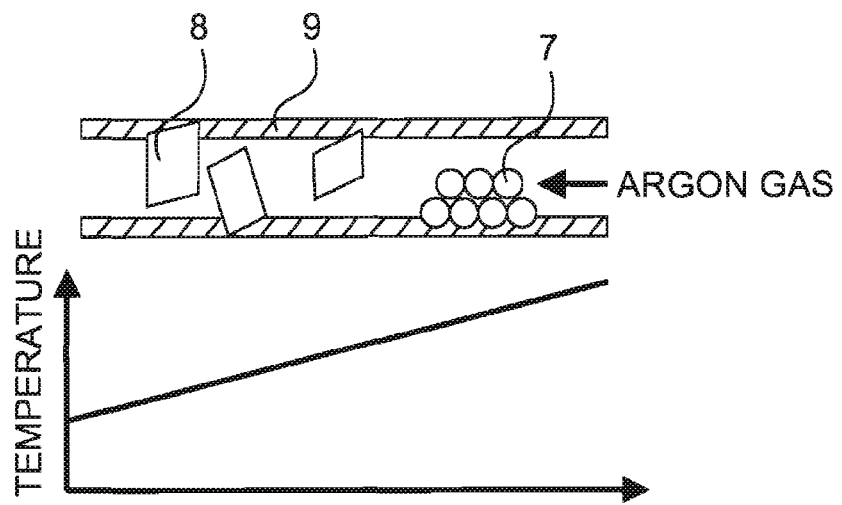
FIG. 4 is an illustration showing a step for manufacturing a monocrystal thin film for the organic thin film transistor obtained in an example 2 thereof.

FIG. 4 illustrates the physical vapor transport method. In this method, first, as shown in FIG. 4, an inactive gas such as argon gas was introduced into a tubular electric furnace 9, which allows temperature gradient such that an upper stream side of a gas flow in the tubular electric furnace 9 is at a higher temperature. Next, on the higher-temperature side was placed a powdery organic semiconductor material 7 such as the anti-type bis(benzo[4,5]thieno)[2,3-b: 2'3'-e][1,4]dithiin. Temperature was adjusted such that the anti-type bis(benzo [4,5]thieno)[2,3-b: 2'3'-e][1,4]dithiin was gradually sublimed to be crystallized on a low-temperature portion of a lower stream side thereof. Furthermore, an obtained crystal 8 was placed again on the upper stream side to be repeatedly recrystallized a couple of times (e.g. three times), whereby a high-grade organic semiconductor crystal could be produced. In this manner, a flat-surface and normal monocrystal of the anti-type bis(benzo[4,5]thieno)[2,3-b: 2'3'-e][1,4]dithiin was obtained.

Manufacturing of Substrate

Figure 5A:
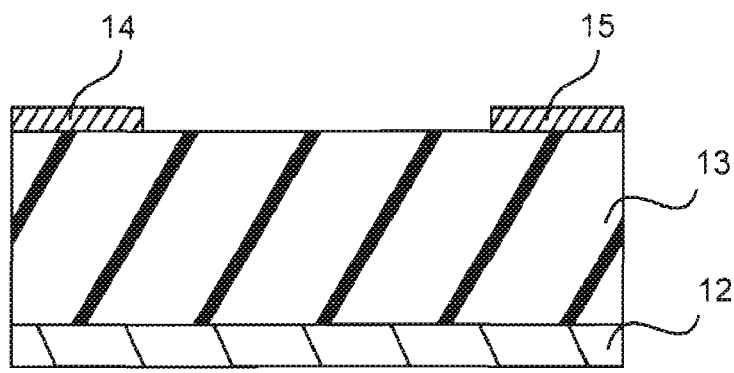
FIGS. 5A to 5C are illustrations showing steps for manufacturing the organic thin film transistor of the example 2.
Figure 5B:
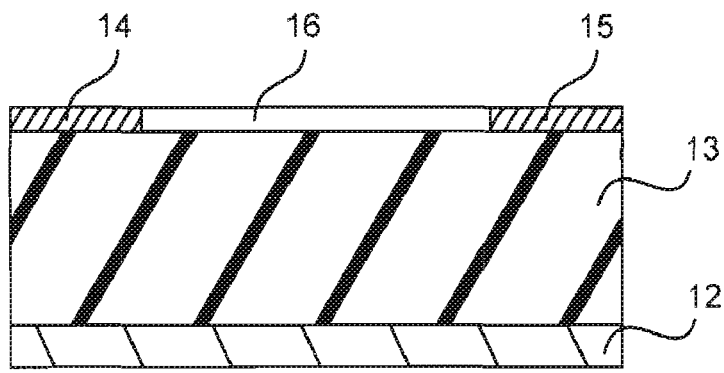
Figure 5C:
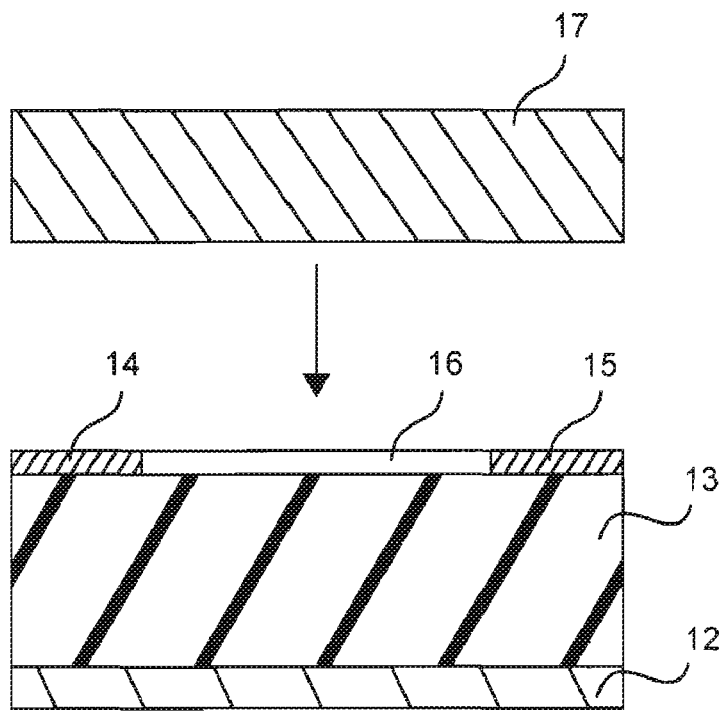

As shown in FIG. 5A, a monocrystal silicon substrate (silicon wafer) was prepared that has a doped impurity. A region having conductivity due to the doped impurity was used as the gate electrode 12. FIGS. 5A to 5C do not include the illustration of the substrate 11. Next, a surface of the conductive silicon wafer was oxidized to form the gate insulation film 13 made of silicon oxide with a thickness of approximately 500 nm. Then, on the gate insulation film 13 was deposited a gold layer having a thickness of approximately 10 nm by vacuum vapor deposition. After that, patterning of the layer was performed by etching and lithography to form the source electrode 14 and the drain electrode 15. The distance between the electrodes 14 and 15 was set to be, for example, approximately 5 μm.

As shown in FIG. 5B, on the gate insulation film 13 was formed the modifying film 16 made of a silane compound. Forming the modifying film 16 allows the threshold voltage (Vth) of the organic thin film transistor to be controlled at a desired value. The used silane compound was $CF_3(CF_2)_7(CH_2)_2Si(OC_2H_5)_3$. Although spin coating was used to form the modifying film 16, another liquid phase coating method such as dipping or gas phase coating such as CVD may be used.

As shown in FIG. 5C, the organic semiconductor thin film 17 made of the monocrystal obtained by the step of FIG. 4 was bonded onto the modifying film 16 by a natural electrostatic attraction to manufacture the organic thin film transistor 10. The transistor obtained by the above method has no crystal grain boundary, so that its surface contacting with the gate insulation film 13 is flat on a molecular scale.

Experimentation Results

Figure 6:
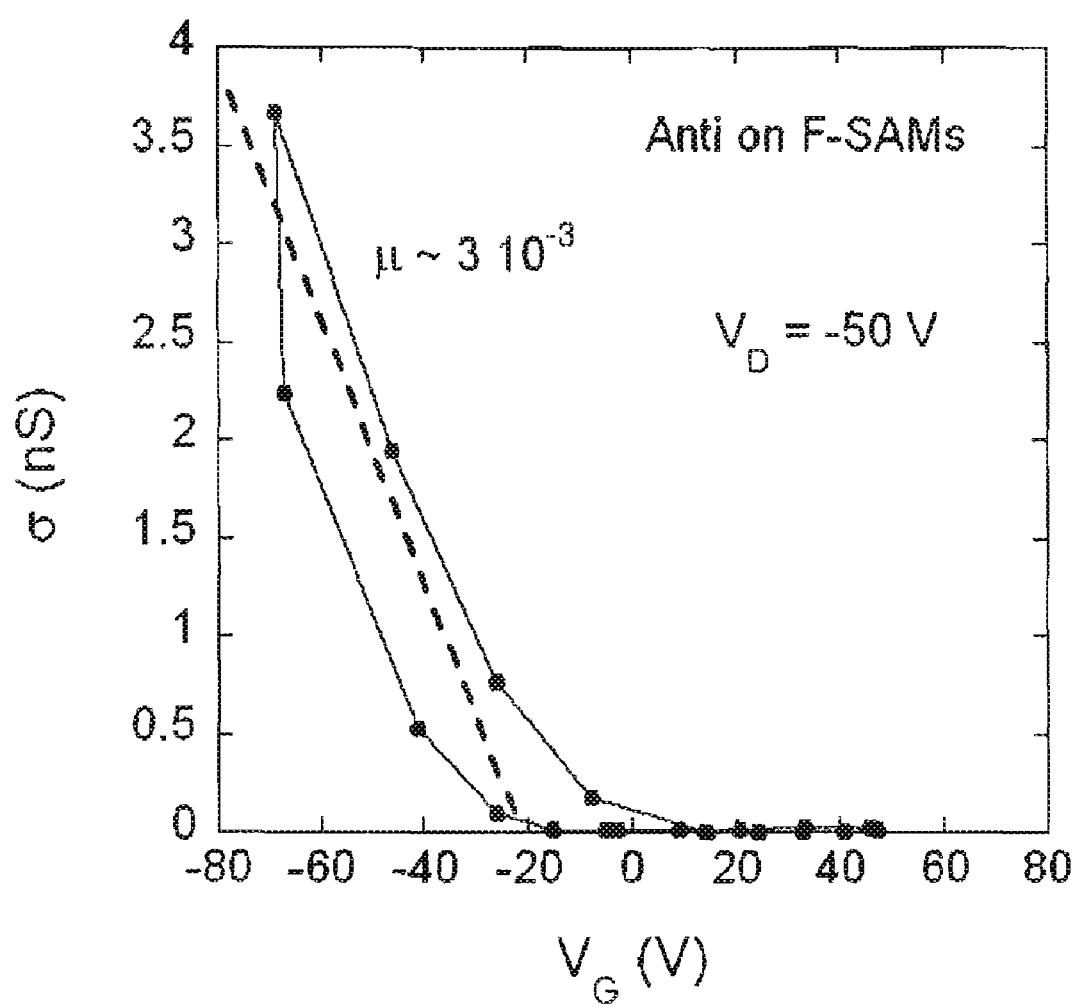
FIG. 6 is a graph showing the characteristics of conductivity (σ) versus gate voltage ($V_G$) of the organic thin film transistor of the example 2.

Next, measurements were performed to investigate transfer characteristics of the organic field effect transistor 10 according to the above embodiment. FIG. 6 shows the transfer characteristics (conductivity σ varying with gate voltage $V_G$) of the organic field effect transistor 10 obtained when $V_D$ drain voltage ($V_D$) was fixed to be −50V.

Results shown in a graph of FIG. 6 demonstrated that the anti-type bis(benzo[4,5]thieno)[2,3-b: 2'3'-e][1,4]dithiin has p-type semiconductor characteristics with a negative threshold voltage. From the graph of FIG. 6, it was calculated that the mobility μ of the device was $3.0 \times 10^{-3}$ cm$^2$/Vs and the threshold voltage Vth was approximately −20V.

In the example 2, the organic semiconductor monocrystal was first produced and then bonded to the substrate. However, the example 2 may be implemented in the same manner as in the example 1. In addition, the organic semiconductor material of the example 1 may also be produced in the same manner as in the example 2.

Next will be described a method for synthesizing each of the compounds. Hereinafter, the bis(benzo[4,5]thieno)[2,3-b: 3'2'-e][1,4]dithiin is referred to as a target compound 1, and the bis(benzo[4,5]thieno)[2,3-b: 2'3'-e][1,4]dithiin is referred to as a target compound 5. Exemplary known methods for producing the target compounds are disclosed in the non-patent related art mentioned above.

Outline of Synthetic Method for Target Compound 1

In a method shown below, bis(benzo[4,5]thieno)[2,3-b: 3'2'-e][1,4]dithiin (target compound 1) is synthesized from benzo[b]thiophene (compound 2) via 3-bromobenzo[b]thiophene (compound 3) and 3,3'-bis(benzo[b]thienyl)sulfide (compound 4).

Known Method

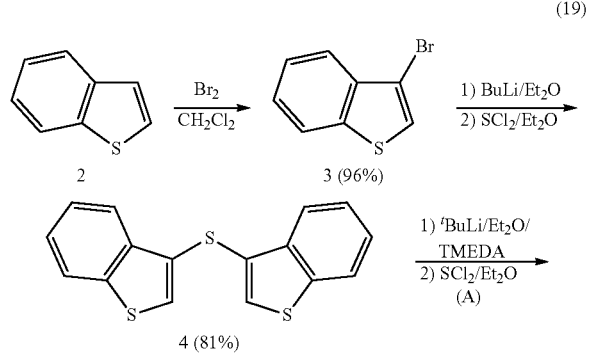

(19)

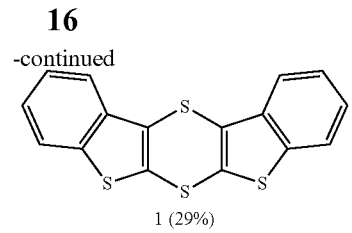

1 (29%)

In the above synthetic method, using the compound 4 as a raw material allowed synthesis of the target compound 1 with a yield of 99%. In the above method, the compound 4 was dilithiated using tert-butyllithium/tetramethylethylenediamine (t-BuLi/TMEDA) and then reacted with sulfur dichloride to produce the target compound 1. However, in the above method, it seems that there was a problem in the step of generating a dianion in molecules by deprotonation with an organic base, which resulted in the low yield. This is probably due to a change in the acidity of protons during the process of conversion from a neutral molecule into a monoanion and then into a dianion. Shown below will be the synthesis of the compound 1 by an improved method. The improved method allowed an increase up to 44% in the yield.

Improved Method

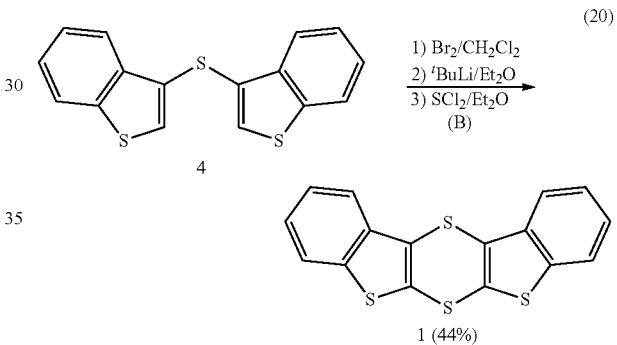

(20)

1 (44%)

In the improved method, after a dibromo compound was produced by reacting the compound 4 with two mol-equivalent of bromine, the compound (unpurified) was converted into a dianionic compound using t-BuLi and then reacted with sulfur dichloride so as to give the target compound 1. In this method, without going through a step of direct deprotonation of the compound 4, the dianionic compound could be produced through a metal-halogen exchange reaction. Accordingly, the synthetic reaction seems to have proceeded without depending on the change in the proton acidity. The improved method showed its extreme usefulness in the yield increase up to 44% from 29% obtained by the known method.

Described below is a synthesis of the target compound 1 by each of the known method (step A) and the improved method (step B).

Step A

The compound 4 (298 mg, 1.0 mmol) and a stir bar were placed in a 100-ml three-neck flask and nitrogen replacement was carried out in the reaction vessel. A mixture of $Et_2O$ (50 ml) and TMEDA (0.3 ml, 2.0 mmol) was added and the reaction vessel was cooled to −30° C. Then, t-BuLi (1.43M pentane solution, 1.4 ml, 2.0 mmol) was added and the mixture was stirred at −30° C. for 1 hour. Next, sulfur dichloride (0.063 ml, 1.0 mmol) diluted with $Et_2O$ (30 ml) was slowly dropped in the mixture. After completion of the dropping, the reaction mixture was stirred at a room temperature for 18 hours. Then, water was poured into the reaction solution and hydrochloric acid was added to adjust the pH of the solution to 1.0. After being extracted with methylene chloride, the organic layer was dried over anhydrous magnesium sulfate and filtered. The solvent was removed by a rotary evaporator. Through silica gel column chromatography using hexane as a developing solvent, the target compound 1 (95 mg, 0.289 mmol, 29%) was separated and purified. The target compound 1 obtained was a colorless crystal having a melting point of 195.0 to 196.0° C. Structural data thereof were as follows:

$^1$H NMR (400 MHz, CDCl$_3$) δ 7.34 (t, 2H, J=7.8 Hz, ArH), 7.41 (t, 2H, J=7.8 Hz, ArH), 7.71 (d, 2H, J=7.8 Hz, ArH), 7.76 (d, 2H, J=7.8 Hz, ArH); $^{13}$C NMR (101 MHz, CDCl$_3$) δ 120.9, 122.5, 125.0, 125.1, 126.4, 129.9, 136.5, 141.0; IR (KBr) ν: 1423, 1314, 1250, 744, 720 cm$^{-1}$; MS (70 eV) m/z 328 (M$^+$); Anal. Calcd for C$_{16}$H$_8$S$_4$: C, 58.50; H, 2.45%. Found: C, 58.18; H, 2.78%.

Step B

The compound 4 (3.219 g, 10.786 mmol) and a stir bar were placed in a 200-ml three-neck flask and dissolved in 100 ml of CH$_2$Cl$_2$. Then, the reaction vessel was cooled to 0° C. Bromine (1.13 ml, 22.0 mmol) diluted with 20 ml of CH$_2$Cl$_2$ was slowly dropped into the vessel for 80 minutes. After completion of the dropping, the mixture in the reaction vessel was stirred at a room temperature for 14 hours. An aqueous solution of sodium hydrogen sulfite was poured into the reaction vessel to wash the organic phase. The reaction solution was separated by a separatory funnel and the organic layer was dried over anhydrous magnesium sulfate and filtered. Then, the solvent was removed by a rotary evaporator. Through silica gel column chromatography using hexane as a developing solvent, a light yellow solid (4.025 g, 8.822 mmol, 82%) was separated and purified. The solid seemed to be 2,2'-dibromo-3,3'-bis(benzo[b]thienyl)sulfide. The light yellow solid (456 mg, 1.0 mmol) and a stir bar were placed in a 200-ml three-neck flask and nitrogen replacement was carried out in the reaction vessel. Next, anhydrous Et$_2$O (80 ml) was added and the reaction vessel was cooled to −30° C. Then, t-BuLi (1.6M pentane solution, 1.25 ml, 2.0 mmol) was added and the mixture was stirred at −30° C. for 40 minutes. Next, sulfur dichloride (0.063 ml, 1.0 mmol) was slowly dropped in the mixture. After completion of the dropping, the reaction mixture was stirred at a room temperature for 11 hours. The solvent was removed by the rotary evaporator. Water was poured in the obtained reaction mixture and hydrochloric acid was added to adjust the pH of the solution to 1.0. After being extracted with chloroform, the organic layer was dried over anhydrous magnesium sulfate and filtered. The solvent was removed by the rotary evaporator. Through the silica gel column chromatography using hexane as a developing solvent, the target compound 1 (145 mg, 0.441 mmol, 44%) was separated and purified as a light yellow solid. Structural data of the compound were as follows:

$^1$H NMR (400 MHz, CDCl$_3$) δ 7.26-7.33 (m, 4H, ArH), 7.66-7.70 (m, 2H, ArH), 7.76-7.80 (m, 2H, ArH); $^{13}$C NMR (101 MHz, CDCl$_3$) δ 121.4, 121.9, 122.8, 124.6, 125.2, 125.3, 138.9, 139.1.

Outline of Synthetic Method for Target Compound 5

As shown below, bis(benzo[4,5]thieno)[2,3-b: 2'3'-e][1,4]dithiin (target compound 5) is synthesized from a benzo[b]thiophene (compound 2) via 2-melcaptobenzo[b]thiophene (compound 6) and 2,3'-bis(benzo[b]thienyl)sulfide (compound 7).

Known Method

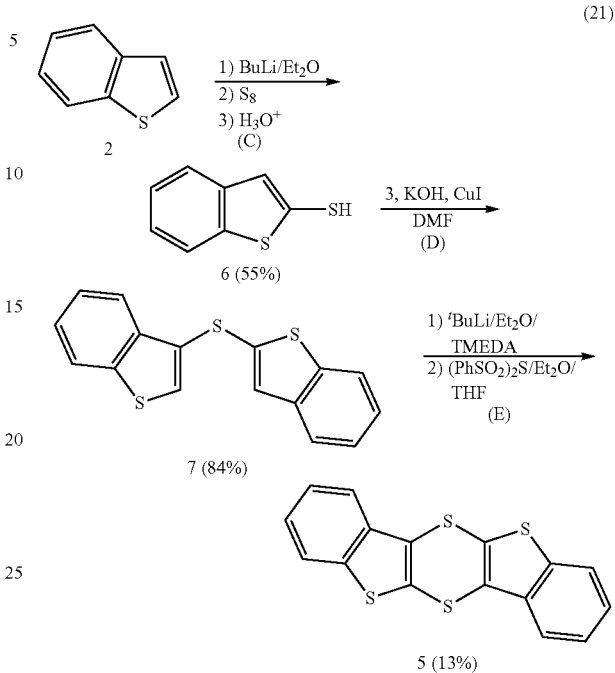

In the known method, going through the synthetic steps of the above compounds 6 and 7, the target compound 5 was synthesized with a yield of 13%. In the known method, a synthesis from the compound 2 as an initial raw material into the compound 6 resulted in a yield of 55%, and then a synthesis from the compound 6 into the compound 7 resulted in a yield of 84%. Consequently, a total yield up to the synthesis of the compound 7 was 46%. The almost-intermediate yield rate seems to imply that instability of the compound 6 in air caused a problem during a purification process of the compound 6 or a pre-reaction process of the compound 7. Meanwhile, the improved method could increase the yield of the compound 7 by replacement of the intermediate compound and also could establish a method for mass synthesis of the target compound 5.

Improved Synthetic Method for Compound 7

As shown below, in the improved method, the compound 7 was synthesized from the compound 2 via 2-acetylthiobenzo[b]thiophene (compound 8).

Improved Method

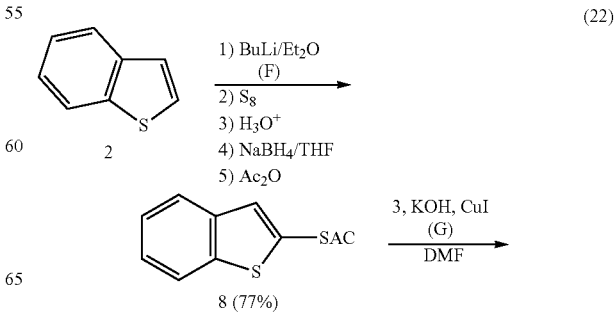

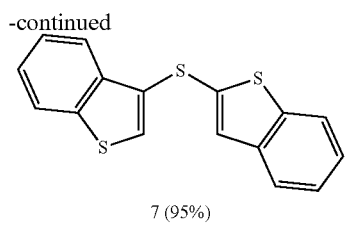

7 (95%)

In the improved method, a thiol group, which is a main cause of instability of the compound 6, was replaced by a relatively stable acetylthio group to obtain the compound 8, which was used as a synthetic equivalent of the compound 6. After lithiation of benzo[b]thiophene using BuLi, elemental sulfur was added. Then, through a series of steps of protonization, hydride reduction with an inorganic reducing agent and acetylation with acetic anhydride, the compound 8 was isolated as a stable colorless crystal with a yield of 77%. Next, the compound 8 was reacted with 3-bromobenzo[b]thiophene (compound 3), copper iodide and potassium hydroxide to synthesize the compound 7 with a yield of 95%. In the improved method, instead of the unstable compound 6, going through the synthesis of the compound 8 as the stable synthetic equivalent, a total yield up to the synthesis of the compound 7 increased up to 73% from 46% obtained by the known method. This demonstrated that the improved method is extremely useful. Furthermore, although the compound 6 causes bad smell, the compound 8 has no smell. Accordingly, in terms of handling as well as yield, the present method for synthesizing the target compound 7 via the compound 8 is significantly effective.

Improved Synthetic Method for Target Compound 5

In the known method, the synthesis from the compound 7 as a raw material into the compound 5 resulted in the low yield of 13%. In addition, in this case, sulfurization and cyclization reactions were performed using an expensive reagent, bis(phenylsulfonyl)sulfide. In the reaction system, the reagent for the sulfurization and cyclization is expensive and 90 wt % thereof is discarded, the method seems unsuitable for mass synthesis. Hereinafter will be shown an improved method for synthesizing the target compound 5.

Improved Method

Formula 23

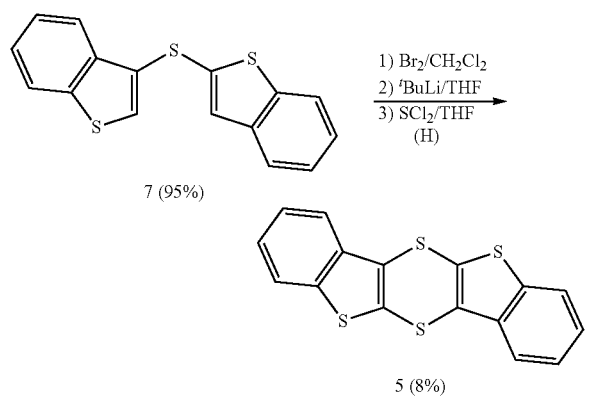

The improved method is provided in consideration of the following two points to design a reaction system enabling mass synthesis of the target compound. A first improved point is to increase the synthesis rate of a dianionic compound by bromination of the compound 7 and a sequential metal-halogen exchange.

That allows dilithiation without going through deprotonation due to acidity difference between protons at different positions. A second improved point is to use sulfur dichloride, which is inexpensive as a reagent. Experimentation steps were as follows. Two equivalents of bromine were added to the compound 7 to give a dibromo compound. Then, after dilithiation using t-BuLi, sulfurization and cyclization of the compound were performed using sulfur dichloride, whereby the target compound 5 was synthesized with a yield of 8%. In terms of the yield rate, the improved method is inferior to the known method. However, since the improved method uses the inexpensive reagent, it is significantly effective in achieving mass synthesis of the compound.

Described below will be the details of steps G to H up to the synthesis of the target compound 5 in each of the known method and the improved method.

Step C: Synthesis of Compound 6

The compound 2 (13.420 g, 100.0 mmol) and a stir bar were placed in a 300-ml three-neck flask and nitrogen replacement was carried out in the reaction vessel. Next, anhydrous $Et_2O$ (200 ml) was added and the reaction vessel was cooled to −15° C. Then, n-BuLi (2.44M hexane solution, 40.98 ml, 110.0 mmol) was added and the mixture was stirred at −15° C. for 30 minutes. Next, elemental sulfur (7.697 g, 240.0 mmol) was slowly added and the mixture was stirred at a room temperature for 11 hours. Water was poured into the reaction mixture and hydrochloric acid was added to adjust the pH of the solution to 1.0. After being extracted with $CH_2Cl_2$, the organic layer was dried over anhydrous magnesium sulfate and filtered. Then, the solvent was removed by a rotary evaporator. The reaction mixture obtained was dissolved into 100 ml of tetrahydrofuran (THF). After slowly adding sodium tetrahydroborate (3.782 g, 100.0 mmol) at a room temperature, the mixture was stirred for 1 hour as it was. Next, water was poured into the reaction solution and hydrochloric acid was added to adjust the pH of the solution to 1.0. After being extracted with $Et_2O$, an aqueous solution of 5.0M sodium hydroxide was added to the organic phase to make the mixture basic. Then, the aqueous phase was separated and hydrochloric acid was added to the aqueous phase to adjust its pH to 1.0. After being extracted with $CH_2Cl_2$, the organic layer was dried over anhydrous magnesium sulfate and filtered. Then, the solvent was removed by the rotary evaporator. Through silica gel column chromatography using hexane as a developing solvent, the compound 6 (9.156 g, 55.07 mmol, 55%) was separated and purified as a white solid. Structural data of the compound were as follows:

$^1$H NMR (400 MHz, $CDCl_3$) δ 3.67 (d, 1H, J=1.0 Hz, SH), 7.26 (brs, 1H, ArH), 7.29 (dd, 1H, J=7.5, 1.7 Hz, ArH), 7.30 (dd, 1H, J=7.2, 1.4 Hz, ArH), 7.65 (dd, 1H, J=6.9, 2.0 Hz, ArH), 7.70 (dd, 1H, J=7.0, 1.8 Hz, ArH).

Step D: Synthesis of Compound 7

The compound 6 (6.291 g, 37.84 mmol), the compound 3 (8.064 g, 37.84 mmol), copper iodide (7.207 g, 37.84 mmol), potassium hydroxide (2.123 g, 37.84 mmol) and a stir bar were placed in a 100-ml three-neck flask and nitrogen replacement was carried out in the reaction vessel. Next, 37.84 ml of anhydrous dimethylformamide (DMF) was added and the mixture was stirred at 130 to 140° C. for 30 hours. Water was poured in the reaction solution and hydrochloric acid was added to adjust the pH of the solution to 1.0. After the insolubles were filtered off under suction, the reaction solution was extracted with $CH_2Cl_2$ and the organic layer was dried over anhydrous magnesium sulfate and filtered.

Then, the solvent was completely removed by a rotary evaporator and a suction pump. Colorless crystal flakes of the compound 7 (9.507 g, 31.85 mmol, 84%) were separated and purified from the obtained reaction mixture by silica gel column chromatography using hexane as a developing solvent. The compound 7 obtained had a melting point of 83.0 to 84.0° C. Structural data thereof were as follows:

$^1$H NMR (400 MHz, CDCl$_3$) δ 7.23 (td, 1H, J=7.5, 1.4 Hz, ArH), 7.28 (td, 1H, J=7.5, 1.4 Hz, ArH), 7.31 (s, 1H, ArH), 7.37 (td, 1H, J=6.2, 1.9 Hz, ArH), 7.40 (td, 1H, J=6.2, 1.8 Hz, ArH), 7.62 (td, 2H, J=7.5, 1.4 Hz, ArH), 7.69 (s, 1H, ArH), 7.85 (dd, 1H, J=6.2, 1.9 Hz, ArH), 7.97 (dd, 1H, J=6.2, 1.8 Hz, ArH) $^{13}$C NMR (101 MHz, CDCl$_3$) δ 121.8, 122.7, 122.9, 123.0, 124.3, 124.4, 124.8, 124.95, 125.02, 126.6, 130.8, 136.6, 138, 4, 139.7, 139.8, 141.3; IR (KBr) v: 1422, 833, 760, 751, 733 cm$^{-1}$; MS (70 eV) m/z298 (M$^+$); Anal. Calcd for C$_{16}$H$_{10}$S$_3$: C, 64.39; H, 3.38%. Found: C, 64.54; H, 3.44%.

Step E: Synthesis of Target Compound 5

The compound 7 (298 mg, 1.0 mmol) and a stir bar were placed in a 100-ml three-neck flask and nitrogen replacement was carried out in the reaction vessel. Et$_2$O (30 ml) and TMEDA (0.30 ml, 2.0 mmol) were added and the reaction vessel was cooled to −30° C. Then, t-BuLi (1.43M pentane solution, 1.4 ml, 2.0 mmol) was added and the mixture was stirred at −30° C. for 1 hour. Next, bis(phenylsulfonyl)sulfide was dissolved into Et$_2$O (30 ml) and THF (15 ml), and the mixture was slowly dropped in the reaction solution. After completion of the dropping, the solution was stirred at a room temperature for 18 hours. Water was poured in the reaction mixture and hydrochloric acid was added to adjust the pH of the solution to 1.0. After being extracted with methylene chloride and chloroform, the organic layer was dried over anhydrous magnesium sulfate and filtered. Then, the solvent was removed by a rotary evaporator. Through silica gel column chromatography using hexane as a developing solvent, the target compound 5 (43 mg, 0.131 mmol, 13%) was separated and purified as a colorless crystal. The compound 5 obtained had a melting point of 207.0 to 208.3° C. Structural data thereof were as follows:

$^1$H NMR (400 MHz, CDCl$_3$) δ 7.34 (t, 2H, J=7.4 Hz, ArH), 7.41 (t, 2H, J=7.4 Hz, ArH), 7.69 (d, 2H, J=7.9 Hz, ArH), 7.73 (d, 2H, J=8.0 Hz, ArH); $^{13}$C NMR (101 MHz, CDCl$_3$) δ 120.6, 122.5, 124.9, 125.0, 125.7, 131.3, 136.3, 140.9; IR (KBr) v: 1478, 1454, 1419, 1251, 1018, 910, 741, 718 cm$^{-1}$; MS (70 eV) m/z 328 (M$^+$); Anal. Calcd for C$_{16}$H$_8$S$_4$: C, 58.50; H, 2.45%. Found: C, 58.48; H, 2.57%.

Step F: Synthesis of Compound 8

The compound 2 (13.420 g, 100.0 mmol) and a stir bar were placed in a 300-ml three-neck flask and nitrogen replacement was carried out in the reaction vessel. Anhydrous Et$_2$O (200 ml) was added and the reaction vessel was cooled to −15° C. Then, n-BuLi (2.55M hexane solution, 43.14 ml, 110.0 mmol) was added and the mixture was stirred at −15° C. for 1 hour. Next, elemental sulfur (3.848 g, ⅛S$_8$: 110.0 mmol) was slowly added and the mixture was stirred at a room temperature for 4 hours. Water was poured into the reaction solution and hydrochloric acid was added to adjust the pH value of the solution to 1.0. After being extracted with CH$_2$Cl$_2$, the organic layer was dried over anhydrous magnesium sulfate and filtered. Then, the solvent was removed by a rotary evaporator. The obtained reaction mixture was dissolved into THF (100 ml) and then sodium tetrahydroborate (1.891 g, 50.0 mmol) was slowly added at a room temperature. The mixture was stirred for 30 minutes as it was. Next, acetic anhydride (18.8 ml, 200.0 mmol) was slowly added and the mixture solution was stirred at a room temperature for 30 minutes. Water was poured into the reaction solution. After being extracted with CH$_2$Cl$_2$, the organic layer was dried over anhydrous magnesium sulfate and filtered. Then, the solvent was removed by the rotary evaporator. Methylene chloride was added to the obtained reaction mixture and an insoluble solid was filtered off. Next, recrystallization was repeated twice with methylene chloride, whereby a colorless crystal of the compound 8 (11.885 g+4.157 g, 77.014 mmol, 77%) was separated and purified. The compound 8 had a melting point of 91.5 to 92.0° C. and structural data thereof were as follows:

$^1$H NMR (400 MHz, CDCl$_3$) δ 2.45 (s, 3H, Acetyl), 7.357 (t, 1H, J=6.6 Hz, ArH), 7.365 (t, 1H, J=6.5 Hz, ArH), 7.43 (s, 1H, thiophene-H), 7.78 (dd, 1H, J=6.4, 3.1 Hz, ArH), 7.81 (dd, 1H, J=6.8, 3.6 Hz, ArH); $^{13}$C NMR (101 MHz, CDCl$_3$) δ 29.8, 122.1, 124.0, 124.5, 125.3, 127.1, 132.4, 139.3, 143.2, 193.2; IR (KBr) v: 1703, 1107, 955, 750, 612 cm$^{-1}$; MS (70 eV) m/z 208 (M$^+$); Anal. Calcd for C$_{10}$H$_8$OS$_2$: C, 57.66; H, 3.87%. Found: C, 57.85; H, 3.83%.

Step G: Synthesis of Compound 7

The compound 8 (10.415 g, 50.00 mmol), the compound 3 (10.655 g, 50.00 mmol), copper iodide (9.525 g, 50.00 mmol), potassium hydroxide (5.611 g, 100.00 mmol) and a stir bar were placed in a 300-ml two-neck flask and nitrogen replacement was carried out in the reaction vessel. Next, anhydrous DMF (50.00 ml) was added and the mixture was stirred at 130 to 140° C. for 34 hours. Water was poured in the reaction solution and hydrochloric acid was added to adjust the pH of the solution to 1.0. After the insolubles were filtered off under suction, the reaction solution was extracted with CH$_2$Cl$_2$ and the organic layer was dried over anhydrous magnesium sulfate and filtered. Then, the solvent was removed by a rotary evaporator. The obtained reaction mixture was absorbed onto silica gel using CH$_2$Cl$_2$ and dried up. The residue was eluted with hexane to obtain a white solid. The solid was recrystallized using hexane and then subjected to silica gel column chromatography using hexane of the filtrate as a developing solvent. Thereby, colorless crystal flakes of the compound 7 (8.582 g+5.521 g, 47.25 mmol, 95%) were separated and purified.

Step H: Synthesis of Target Compound 5

The compound 7 (5.969 g, 20.0 mmol) and a stir bar were placed in a 300-ml three-neck flask and dissolved in 100 ml of CH$_2$Cl$_2$. Bromine (2.06 ml, 40.0 mmol) diluted with 50 ml of CH$_2$Cl$_2$ was slowly dropped in the vessel. After completion of the dropping, the mixture solution in the reaction vessel was stirred at a room temperature for 30 hours. Sodium hydrogen sulfite aqueous solution was poured in the reaction vessel to wash the organic phase. The reaction solution was separated by a separatory funnel and the organic layer was dried over anhydrous magnesium sulfate and filtered. Then, the solvent was removed by a rotary evaporator. The obtained solid was 5.926 g, of which 5.750 g and a stir bar were placed in a 300-ml three-neck flask and nitrogen replacement was carried out in the reaction vessel. Then, anhydrous THF (100 ml) was added and the reaction vessel was cooled to −78° C. Next, t-BuLi (1.59M pentane solution, 31.706 ml, 50.412 mmol) was added and the mixture was stirred at −78° C. for 10 minutes. Sulfur dichloride (0.791 ml, 12.603 mmol) diluted with dried THF (50 ml) was slowly dropped in the mixture. After completion of the dropping, the reaction mixture was stirred at a room temperature for 18.5 hours. Then, water was poured in the reaction solution and hydrochloric acid was added to adjust the pH of the solution to 1.0. After extraction with CH$_2$Cl$_2$, the organic layer was dried over anhydrous magnesium sulfate and filtered. Then, the solvent was removed by a rotary evaporator. The residue was recrystallized, twice from CH$_2$Cl$_2$ to give a light yellow crystal (38 mg+464 mg, 8%) as the target compound 5. The target compound 5 had a melting point of 207.0 to 208.3° C. and structural data thereof were as follows:

$^{1}$H NMR (400 MHz, CDCl$_3$) δ 7.34 (t, 2H, J=7.4 Hz, ArH), 7.41 (t, 2H, J=7.4 Hz, ArH), 7.69 (d, 2H, J=7.9 Hz, ArH), 7.73 (d, 2H, J=8.0 Hz, ArH); $^{13}$C NMR (101 MHz, CDCl$_3$) δ 120.6, 122.5, 124.9, 125.0, 125.7, 131.3, 136.3, 140.9; IR (KBr) ν: 1478, 1454, 1419, 1251, 1018, 910, 741, 718 cm$^{-1}$; MS (70 eV) m/z 328 (M$^+$); Anal. Calcd for C$_{16}$H$_8$S$_4$: C, 58.50; H, 2.45%. Found: C, 58.48; H, 2.57%.

What is claimed is:

1. A method for producing bis(benzo[4,5]thieno)[2,3-b:3'2'-e][1,4]dithiin represented by a structural formula 4:

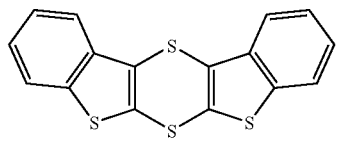

(4)

the method comprising:
(i) dibrominating 3,3'-bis(benzo[b]thienyl)sulfide represented by a structural formula 5:

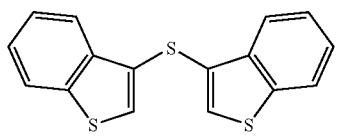

(5)

(ii) dianionizing the dibromo compound; and
(iii) adding sulfur dichloride to react with the dianionic compound.

2. A method for producing bis(benzo[4,5]thieno)[2,3-b:2'3'-e][1,4]dithiin represented by a structural formula 10:

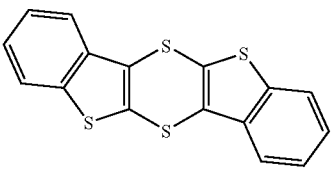

(10)

* * * * *

UNITED STATES PATENT AND TRADEMARK OFFICE
CERTIFICATE OF CORRECTION

| | | |
|---|---|---|
| PATENT NO. | : 7,951,962 B2 | Page 1 of 1 |
| APPLICATION NO. | : 11/850357 | |
| DATED | : May 31, 2011 | |
| INVENTOR(S) | : Takao Nishikawa et al. | |

It is certified that error appears in the above-identified patent and that said Letters Patent is hereby corrected as shown below:

Title Page and Col. 1

Please amend the title page as follows:

Please change "ORGANIC SEMICONDUCTOR COMPOUND, ORGANIC SEMICONDUCTOR THIN FILM, ORGANIC SEMICONDUCTOR COATING LIQUID, ORGANIC THIN FILM TRANSISTOR, METHODS FOR PRODUCING BIS(BENZO[4,5] THIENO)[2,3-B:3'2'-E][1,4]DITHIN AND BIS(BENZO [4,5]THIENO)[2,3-B:2'3'-E][1,4]DITHIIN" to --METHODS FOR PRODUCING BIS(BENZO[4,5]THIENO)[2,3-B:3'2'-E][1,4]DITHIIN AND BIS(BENZO[4,5]THIENO)[2,3-B:2'3'-E][1,4]DITHIIN--.

Signed and Sealed this
Twenty-eighth Day of February, 2012

David J. Kappos
*Director of the United States Patent and Trademark Office*